United States Patent
Bopp et al.

(10) Patent No.: US 9,385,486 B2
(45) Date of Patent: Jul. 5, 2016

(54) SOCKET MODULE, ELECTROSURGICAL DEVICE, AND SET WITH A SOCKET MODULE

(71) Applicant: ERBE Elektromedizin GmbH, Tuebingen (DE)

(72) Inventors: Benjamin Bopp, Ofterdingen (DE); Torsten Zimmermann, Dusslingen (DE); Armin Hauger, Ammerbuch (DE); Juergen Stocker, Nehren (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 0 days.

(21) Appl. No.: 14/817,848

(22) Filed: Aug. 4, 2015

(65) Prior Publication Data

US 2016/0043513 A1 Feb. 11, 2016

(30) Foreign Application Priority Data

Aug. 6, 2014 (EP) .................................... 14179974

(51) Int. Cl.

| H01R 12/70 | (2011.01) |
|---|---|
| H01R 13/66 | (2006.01) |
| A61B 18/12 | (2006.01) |
| H01R 13/15 | (2006.01) |
| H01R 27/00 | (2006.01) |

(Continued)

(52) U.S. Cl.
CPC .............. *H01R 13/665* (2013.01); *A61B 18/12* (2013.01); *A61B 18/1206* (2013.01); *H01R 12/7076* (2013.01); *H01R 13/15* (2013.01); *H01R 27/00* (2013.01); *A61B 2017/00486* (2013.01); *A61B 2018/00178* (2013.01); *H01R 4/4809* (2013.01); *H01R 13/447* (2013.01); *H01R 13/6658* (2013.01); *H01R 24/58* (2013.01); *H01R 24/66* (2013.01); *H01R 2201/12* (2013.01)

(58) Field of Classification Search
CPC .................... H01R 12/7035; H01R 12/7076
See application file for complete search history.

(56) References Cited

U.S. PATENT DOCUMENTS 3,162,788 A * 12/1964 Allen .................. H05K 3/301
174/260
4,003,616 A * 1/1977 Springer ................ H01R 39/64
174/46

(Continued)

FOREIGN PATENT DOCUMENTS

| EP | 1562505 A2 | 8/2005 |
|---|---|---|
| EP | 2033589 A1 | 3/2009 |

(Continued)

*Primary Examiner* — James Harvey
(74) *Attorney, Agent, or Firm* — Fitch, Even, Tabin & Flannery LLP

(57) ABSTRACT

A socket module for an electrosurgical device has a housing (10), at least two connectors (11, 12) each having two contacts (11a, 11b, 12a, 12b). A first connection member (13) electrically connects a first contact (11a) of the first connector (11) to a first contact (12a) of the second connector (12). The first connection member (13) has two contact regions (13a, 13b), of which a first contact region (13a) is connected to the first contact (11a) of the first connector (11) and a second contact region (13b) is connected to the first contact (12a) of the second connector (12). A printed circuit board (15) is arranged in the housing (10) and electrically connected to the first connector. (11) The printed circuit board (15) supports a third contact region (15a, 15b) which connects the first connector (11) to the printed circuit board (15).

18 Claims, 4 Drawing Sheets

(51) Int. Cl.
  *A61B 17/00*    (2006.01)
  *A61B 18/00*    (2006.01)
  *H01R 4/48*     (2006.01)
  *H01R 13/447*   (2006.01)
  *H01R 24/58*    (2011.01)
  *H01R 24/66*    (2011.01)

(56) References Cited

U.S. PATENT DOCUMENTS

| | | | | |
|---|---|---|---|---|
| 5,548,360 A | * | 8/1996 | Uematsu | G03B 7/24 396/208 |
| 8,961,197 B2 | * | 2/2015 | Ferran Palau | H01R 33/06 439/76.2 |
| 2004/0050576 A1 | * | 3/2004 | Chen | H01R 9/0518 174/78 |
| 2004/0097912 A1 | * | 5/2004 | Gonnering | A61B 18/1206 606/34 |
| 2008/0278276 A1 | * | 11/2008 | Banzo | H01H 85/0417 337/186 |
| 2016/0043513 A1 | * | 2/2016 | Bopp | A61B 18/12 439/620.22 |

FOREIGN PATENT DOCUMENTS

| | | |
|---|---|---|
| EP | 2485670 A2 | 8/2012 |
| WO | 2014071184 A1 | 5/2014 |

* cited by examiner

SOCKET MODULE, ELECTROSURGICAL DEVICE, AND SET WITH A SOCKET MODULE

RELATED APPLICATION(S)

This application claims the benefit of European Patent Application No. EP 14179974.2 filed Aug. 6, 2014, the contents of which are incorporated herein by reference as if fully rewritten herein.

TECHNICAL FIELD

The invention relates to a socket module for an electrosurgical device, to an electrosurgical device with such a socket module, and also to a set with a socket module and a removal tool.

BACKGROUND

Electrosurgical devices, for example high-frequency surgical devices, which have a plurality of socket modules for connecting surgical instruments are known from practice. The socket modules form plug-in connections between the electrosurgical instruments and the circuits in the interior of the electrosurgical device. Socket modules which in each case have a plurality of connectors for instruments with different plugs are known from practice for connecting electrosurgical instruments and/or neutral electrodes. With these known socket modules, the connectors in the interior of the housing of the respective module are wired together, which requires time-consuming soldering operations. Thus the assembly times for such socket modules are long, and in addition it must be ensured that the soldered connections can withstand the demands made on the electrical devices, in particular with respect to temperature fluctuations, over the entire life of the devices.

SUMMARY

The object of the invention is to devise a socket module for an electrosurgical device for which the assembly times can be shortened and at the same time the quality of the electrical connections can be ensured. Further, the object of the invention is to devise an electrosurgical device with such a socket module, and also a set with a socket module and a removal tool.

The invention is based on the concept of devising a socket module for an electrosurgical device, wherein the socket module has a housing, at least two connectors with two contacts in each case and also at least a first connection means. The first connection means electrically connects a first contact of the first connector to a first contact of the second connector. The invention is distinguished in that the first connection means has two contact regions, of which a first contact region is connected to the first contact of the first connector and a second contact region is connected to the first contact of the second connector in positive manner and/or in non-positive manner in each case. A printed circuit board is arranged in the housing, which board is electrically connected to the first connector. The printed circuit board has a third contact region which connects the first connector to the printed circuit board in positive manner and/or in non-positive manner.

The invention has various advantages. Owing to the positive and/or non-positive connection, the wiring of the connectors can be at least partially dispensed with, thus considerably shortening the assembly times. Furthermore, potential sources of errors which might arise during soldering are avoided.

The printed circuit board arranged in the housing likewise contributes to the number of connecting cables in the housing being reduced, because the printed circuit board is connected to the first connector in positive manner and/or in non-positive manner.

In conjunction with the first connection means, it is disclosed in concrete terms that the first and second contact regions can be connected in each case in positive manner or in each case in non-positive manner to the respective contact. It is also possible for the first contact region to be connected in positive manner and the second contact region to be connected in non-positive manner to the respective contact, or conversely.

A "positive" connection is to be understood to mean a connection between two connecting parts which at least partially grip into or around one another. This means that the connecting parts cannot be detached even without power transmission, or in the event of power transmission being interrupted. The positive connection may also be combined with a non-positive connection, for example by acting upon the respective connecting parts with a spring force. Purely non-positive connections are possible, in which the static friction between the effective surfaces prevents the parts from becoming detached from one another.

The contact regions ensure both the mechanical holding of the parts which are connected together and the electrical contact.

In a particularly preferred embodiment, a second connection means electrically connects a second contact of the first connector to a second contact of the second connector. The second connection means has two contact regions, of which a first contact region is connected to the second contact of the first connector in positive manner and/or in non-positive manner. A second contact region is connected to the second contact of the second connector in positive manner and/or in non-positive manner or by a material bond. Owing to the second connection means, the wiring costs are reduced still further or the wiring can be dispensed with entirely. Compared with the assembly times for known socket modules, the assembly time for this embodiment can be reduced by approximately 75%.

Expediently, at least the first connection means is connected to the housing. It is also possible to connect both the first and the second connection means to the housing, which achieves simple fixing of the connection means. Preferably the first connection means is connected to a removable cover of the housing, as a result of which the ease of assembly of the socket module is improved further, because the connection of the respective contacts of the first and second connector takes place automatically with the closing of the housing by the cover. The second connection means may be connected to a base of the housing, and is thus spaced apart sufficiently reliably from the first connection means.

The contact regions of the first connection means may form clips and/or flexible tongues which are latched with the first contacts and/or lie against them. There are therefore various possible ways of realising the contact regions. For example, the first and second contact regions of the first connection means may be configured in each case by clips or in each case by flexible tongues. It is also possible to configure one contact region by a clip and the other by a flexible tongue. This applies to the first and second contact regions or respectively conversely. The use of clips has the advantage that a particularly secure connection is produced which is independent of the application pressure of the cover. The advantage of the flexible tongues is that they are particularly simple to produce.

The contact regions of the second connection means may form clips and/or flexible tongues and/or bearing surfaces. The clips are latched with the respective second contacts. The flexible tongues lie against the second contacts and the bearing surfaces are connected to the second contacts by a material bond. Here too, all possible combinations are conceivable. For example, one contact region may be configured as a clip and the other contact region as a bearing surface which is connected to the corresponding contact by a material bond, for example by soldering or welding. In particular if the second connection means is arranged on the base of the housing, a connection by a material bond between the respective contact region and the contact is simple to realise.

In a preferred embodiment, at least the first connection means, in particular the first and second connection means, form(s) a metal strip, on the ends of which the contact regions are provided. The metal strip is simple to produce and can be mounted securely and rapidly in the housing.

Preferably the third contact region forms at least one clip which is connected to the printed circuit board. In a particularly preferred embodiment, the third contact region has two clips which are each connected to the printed circuit board. Thus the wiring of the connectors which has been known hitherto is replaced in a simple manner by a mechanical connection, in particular a plug-in or latch connection.

The contact regions, in particular the clips, may have two jaws arranged opposite one another, which in the holding state are acted upon by a spring force. This achieves secure fixing of the parts which are arranged between the jaws, in particular of the contacts of the connectors.

Expediently, the first connector has a stop which cooperates with an outer edge of the printed circuit board to position the connector. The printed circuit board thus has a dual function. Firstly, it serves electrically to connect the connectors to the circuits in the interior of the electrosurgical device. Secondly, it serves as a mechanical stop in order to position the first connector correctly in the longitudinal direction of the connector. This facilitates the mounting of the first connector.

The first connector may comprise two plugs which form the first and second contacts of the first connector. Such a configuration of the connector is suitable for example for internationally-used cables.

The second connector may comprise a female socket and a ratchet spring, the female socket forming the first contact and the ratchet spring the second contact of the second connector. Such a connector is intended for connecting to a jack plug.

The second connector, in particular the ratchet spring, may be placed on at least one holding pin and be fixed by at least one sleeve-like holding-down means which surrounds the holding pin after assembly. Expediently, two holding pins and two corresponding holding-down means are provided. The fixing of the second connector, in particular of the ratchet spring, by the holding pin and the holding-down means replaces the screw connection known per se with which the ratchet spring is fixed in the housing. This means that the screwing operation which is costly in the prior art can be dispensed with when mounting the ratchet spring. Rather, the connection of the holding pin with the sleeve-like holding-down means automatically produces the connection by placing the cover on.

The invention will be explained in greater detail below with further details with reference to the accompanying schematic drawings. Therein:

DETAILED DESCRIPTION

Figure 1:
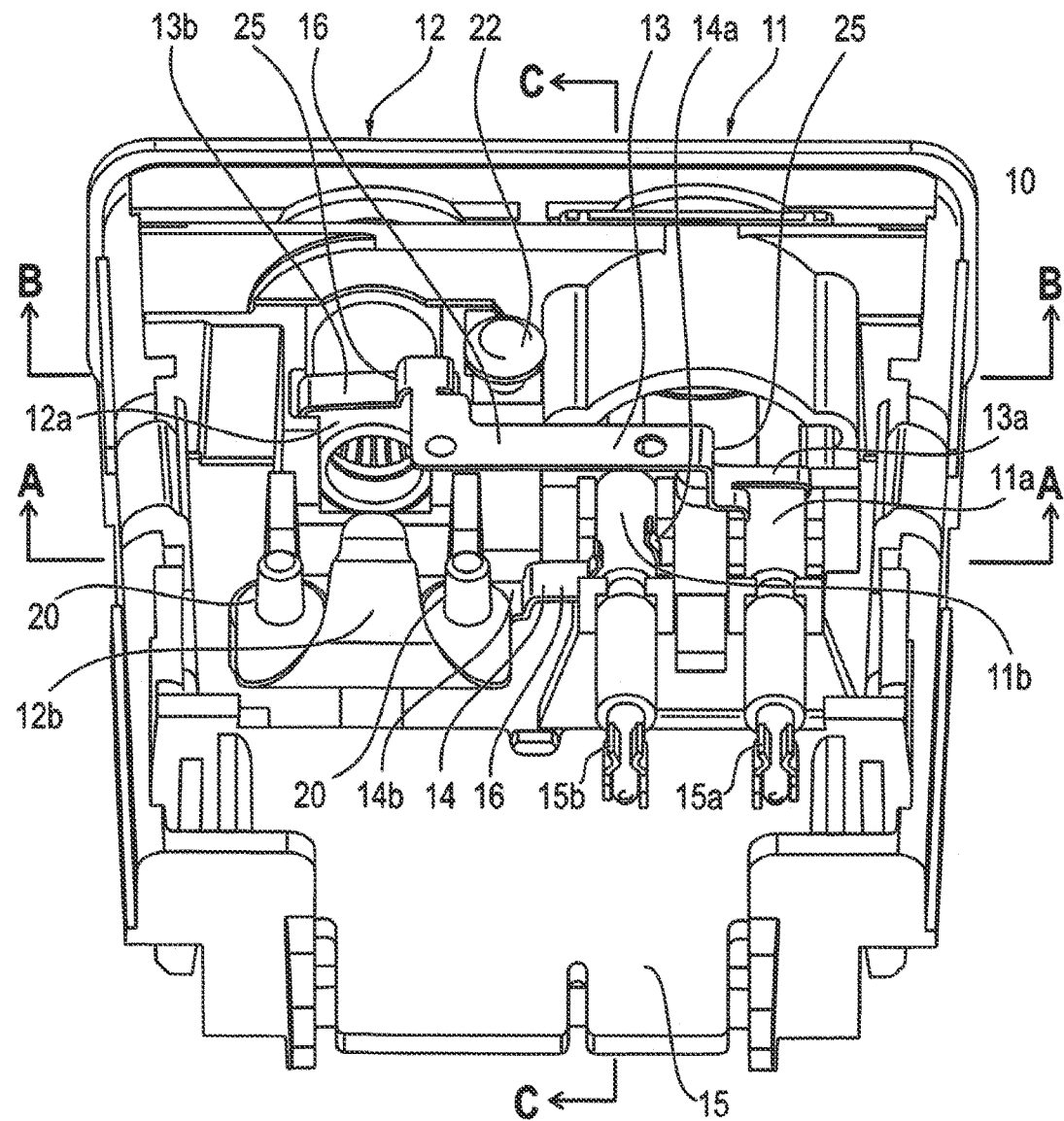
FIG. 1 is a perspective view of a socket module in accordance with an example of embodiment according to the invention in which the cover is removed, the first connection means being shown in the installation position.
Figure 2:
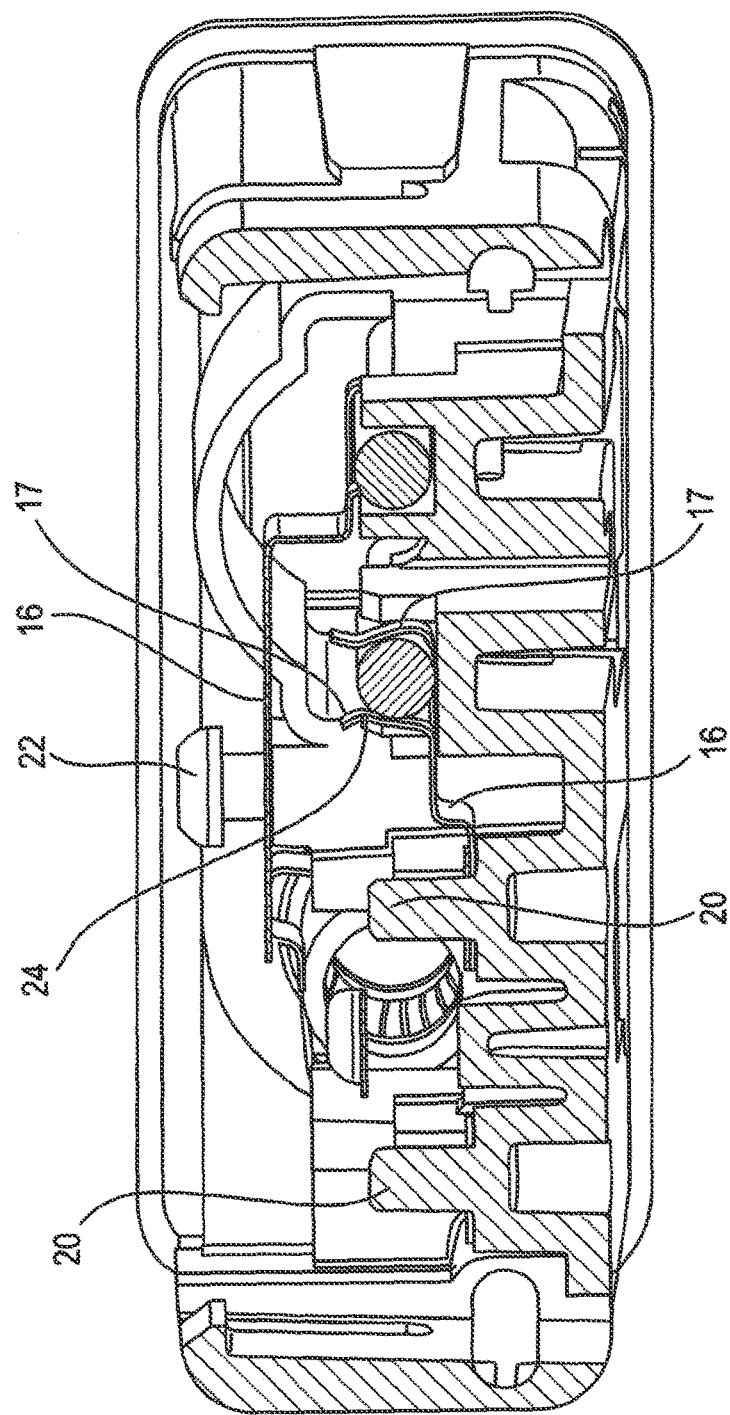
FIG. 2 is a cross-section through the socket module of FIG. 1 along the line A-A.

The socket module illustrated in FIG. 1 is used for connecting neutral electrodes to an electrosurgical device (NE socket module). The invention is not restricted to what are called NE socket modules for neutral electrodes, but can also be applied to other socket modules with which electrosurgical instruments are connected to devices, with various connectors being electrically connected together in the housing of the socket module.

The socket module illustrated in FIG. 1 can be used particularly effectively in combination with the socket insert described in EP 14 154 490, which can be assembled without tools and originates from the applicant. In this respect, the features of the socket insert or socket module described in EP 14 154 490 are likewise realised in the present example of embodiment. Reference is made to EP 14 154 490 with respect to the further details of the socket insert or socket module which can be assembled without tools.

Figure 3:
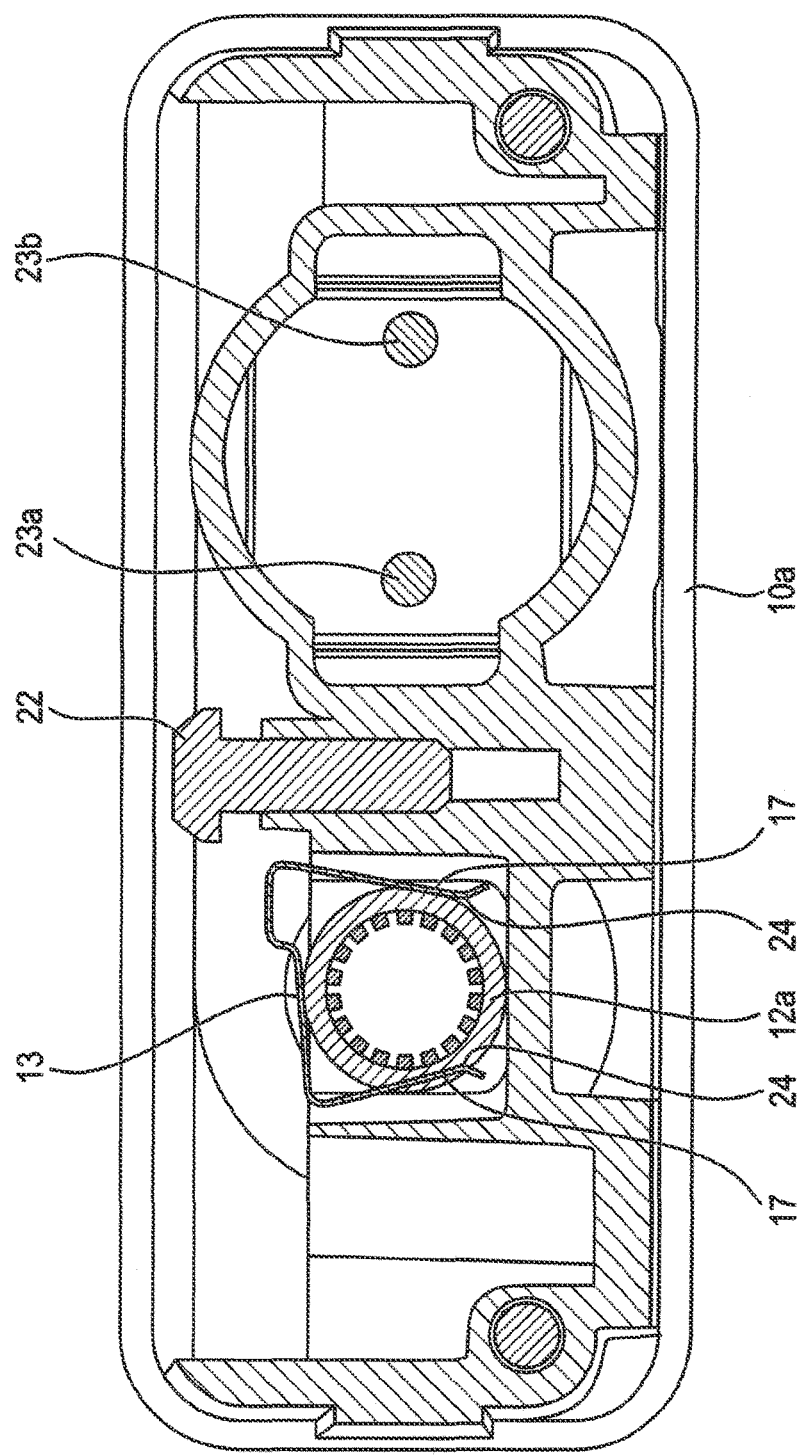
FIG. 3 is a cross-section through the housing of FIG. 1 along the line B-B.

The socket module according to FIG. 1 has a housing 10 with a base 10a and a cover which is removable and is not shown in FIG. 1. The cover can be fixed by the screw 22 illustrated in FIGS. 1-4. Other possible ways of fixing such as for example snap connections of the cover are conceivable. The housing 10 has two connectors 11, 12. The two connectors 11, 12 are suitable for different plug types. In operation, only one connector is ever occupied. For example, the first connector 11 is configured for connection to international cables, and for this purpose has electrical connecting parts, in particular two contact pins 23a, 23b, which are illustrated in FIG. 3. Other electrical connecting parts are possible.

The contact pins 23a, 23b have a dual function. If the first connector 11 is occupied, the contact pins 23a, 23b connect the connected cable to an electronic component, such as the printed circuit board 15, in the interior of the housing. If the second connector 12 is occupied, the contact pins 23a, 23b form part of the electrical connection between the second connector 12 and the further components, in concrete terms the printed circuit board 15. At the same time, the first connector 11 is blocked, so that a cable can be connected only at the second connector 12.

For electrical connection of the second connector 12 and the further components, in concrete terms the printed circuit board 15, the electrical connecting parts, in particular the contact pins 23a, 23b, form the first contact 11a and the second contact 11b of the first connector 11.

The contact pins 23a, 23b are embodied as pin-shaped rotary parts.

The second connector 12 illustrated in FIG. 1 is intended for a jack plug and accordingly has a female socket 12a and also a ratchet spring 12b, which are configured as a first contact 12a or as a second contact 12b respectively of the second connector 12. The female socket will be designated below by the reference numeral 12a, and the ratchet spring by the reference numeral 12b.

The two connectors 11, 12, as illustrated in FIG. 1, are arranged parallel next to one another in the housing 10. The two connectors 11, 12 are accessible through corresponding openings in the front side of the socket module. In the example of embodiment of FIG. 1, securing is provided in the form of a sliding plate, with which one of the two connectors 11, 12 is closed if the other connector 11, 12 is accessible, so that occupation of both connectors simultaneously is avoided.

As can readily be recognised in FIG. 1, the first contact 11a of the first connector 11, i.e. the contact pin 23a, is electrically connected to the first contact 12a of the second connector 12, i.e. the female socket 12a. For this, a first connection means 13 in the form of a metal strip 16 is provided which has two contact regions 13a, 13b. The first contact region 13a is mechanically connected to the contact pin 23a, and the second contact region 13b to the female socket 12a. The connection takes place as a combined positive and non-positive connection, because the contact regions 13a, 13b grip behind the contact pin 23a or the female socket 12a respectively and are additionally acted upon by a holding force, in particular a spring force, which ensures permanent bearing of the contact regions 13a, 13b on the contact pin 23a or the female socket 12a, respectively.

In concrete terms, the contact regions 13a, 13b are embodied in each case as clips 13a, 13b which are latched with the contact pin 23a or with the female socket 12a. For this, the clips have jaws 17 in each case (FIG. 2) which grip at least partially around the first contact pin 23a or the female socket 12a. The jaws 17 in the assembled state are pressed apart from each other by the contact pin 23a or the female socket 12a, so that in the assembled state they exert a spring force on the respective component, i.e. the contact pin 23a or the female socket 12a. The jaws 17 are profiled in such a way that they at least partially grip behind the contact pin 23a or the female socket 12a and thus also bring about a certain positive connection in addition to the non-positive connection.

The distance between the two jaws 17 depends on the diameter of the contact pin 23a or of the female socket 12a. The same applies to the profiling of the end pieces of the two jaws 17, which are inclined inwards as far as a holding edge 24. The holding edge 24 grips behind the contact pin 23a or the female socket 12a, so that, together with the spring force applied by the jaws 17, a secure connection is produced. For simple assembly, the jaws 17 are bent apart from each other in each case after the holding edge 24, so that they do not skew with the contact pin 23a or the female socket 12a when they are placed on during assembly.

The two jaws 17 for the first contact pin 23a are formed in each case in that the metal strip 16 at the corresponding end is divided in the longitudinal direction, with a first jaw 17 being formed by bending over and profiling the divided metal strip 16. The same applies to the second jaw 17, which is formed spaced apart from the first jaw 17 in the longitudinal direction. As can be clearly seen in FIG. 1, the jaws 17 are configured to be offset by the division of the metal strip 16 in the longitudinal direction.

The penetration of the left-hand jaw 17 into the material of the female socket 12a as shown in FIG. 3 is only graphically dictated. In practice, both jaws lie against the outer side of the female socket 12b. The same applies to the other jaw 17 which surrounds the first contact pin 23a.

The metal strip 16 has in the region of the first contact pin 23a a bent edge 25, as a result of which the difference in height between the first contact pin 23a and the cover is compensated. The same applies to the metal strip 16 in the region of the female socket 12a, which strip has a corresponding bent edge 25 there. In the assembled state, the portion of the metal strip 16 between the two bent edges 25 lies against the cover or against the inner side of the cover. To fix the metal strip 16, two pins of the cover protrude through the openings in the metal strip 16 which are illustrated in FIG. 1.

The metal strip 16 in the installed state is angled parallel to the base or parallel to the cover, with one long arm of the metal strip 16 being arranged perpendicular to the longitudinal axis of the first contact pin 23a and a shorter arm of the metal strip 16 being arranged parallel to the longitudinal axis of the female socket 12a. The first contact region 13a is arranged transversely to the longitudinal axis of the first contact pin 23a. The same applies to the second contact region 13b, which is arranged transversely to the longitudinal axis of the female socket 12a. The second contact region 13b is connected to the shorter arm of the metal strip 16. The first contact region 13a is connected to the longer arm of the metal strip 16.

The metal strip 16 forms the electrical connection between the first and second contact, or the female socket 12a and the first contact pin 23a.

The connection of the first contact pin 23a to the printed circuit board 15 which is arranged in the housing (see FIG. 1) likewise takes place in wireless manner. For this, the printed circuit board 15 has a third contact region consisting of the clips 15a, 15b which connects the first connector 11, in concrete terms the first contact pin 23a, in positive and in non-positive manner. For this, a first clip 15a is fastened, in particular soldered, to the printed circuit board 15, which clip is connected on one hand to a pin-like end of the first contact pin 23a and on the other hand to a printed conductor, not shown in FIG. 1, of the printed circuit board. The clip 15a grips around the pin-like end of the first contact pin 23a. For this, the clip 15a has two jaws 17 which, as described above, are profiled. In this respect, reference is made to the features described in conjunction with the clip 13b for the female socket 12a.

Figure 4:
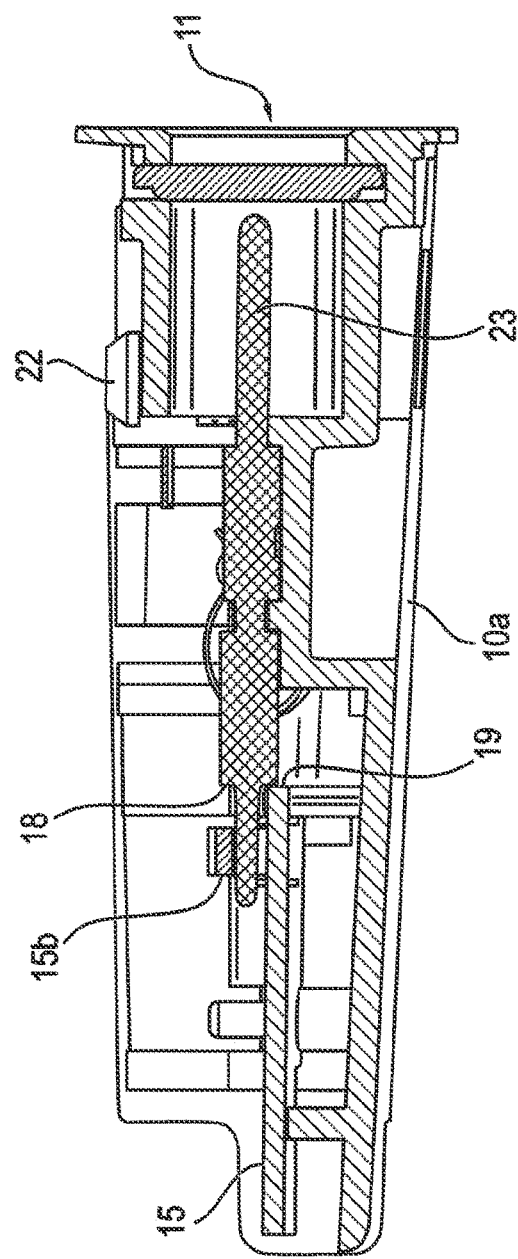
FIG. 4 is a longitudinal section through the socket module of FIG. 1 along the line C-C.

The pin-like end of the first contact pin 23a has a smaller diameter than the contact pin 23a. This achieves a simple connection with a relatively low assembly force between the first connector or the first contact pin 23a respectively and the printed circuit board 15. To simplify the positioning of the first contact pin 23a, the latter has a stop 18 which in the installed state cooperates with an outer edge 19 of the printed circuit board 15 (FIG. 4). This means that the first contact pin 23a can be reliably positioned in the longitudinal direction upon insertion or clipping-in. The same applies to the second contact pin 23b, which forms the second contact 11b of the first connector 11. All the features described in conjunction with the first contact pin 23a and the connection to the printed circuit board 15 are also disclosed in conjunction with the second contact pin 23b.

The second contact pin 23b is electrically connected to the second contact 12b of the first connector, in concrete terms to the ratchet spring 12b. The ratchet spring 12b is aligned in a manner known per se with the female socket 12a and is spaced apart therefrom, so that a two-pole jack plug can be connected to the second connector 12. The electrical connection between the ratchet spring 12b and the second contact pin 23b takes place by a second connection means 14. The second connection means 14 is embodied as a metal strip 16 which is connected to the base 10a of the housing 10 or is arranged on the base 10a. The metal strip 16 or the second connection means 14 has a first contact region 14a which is connected to the second contact pin 23b in positive and in non-positive manner. The first contact region 14a of the second connection means 14 in the example according to FIG. 1 is embodied as a clip analogously to the clip of the first connection means 13. All the features disclosed in conjunction with the clip of the first connection means 13 are also disclosed and claimed in conjunction with the clip of the second connection means 14. The clips are constructed correspondingly. The sole difference between the two clips is that the clip of the second connection means 14, starting from the base 10*a*, is opened upwards, whereas the clip of the first connection means 13 is opened downwards, i.e. opened towards the base 10*a*. The direction of opening is yielded simply from the fact that the second connection means 14 is arranged on the base 10*a*, i.e. that the second contact pin 23*b* has to be introduced into the clip from above. The direction of opening of the clip of the first connection means 13 is determined by the arrangement of the first connection means 13 on the cover, so that a connection of the clip of the first connection means 13 to the first contact pin 23*a* takes place when the cover is placed on.

The connection of the second connection means 14 to the ratchet spring 12*b* takes place by a bearing surface which forms the second contact region 14*b*. The bearing surface lies against the underside of the ratchet spring and this is brought about either in a non-positive manner by a holding force acting on the ratchet spring from above or by a material bond by welding or soldering of the underside of the ratchet spring to the second contact region 14*b*.

The ratchet spring 12*b* is fastened to the base 10*a* of the housing 10 by two holding pins 20, which are also called domes. In the assembled state, the two holding pins 20 cooperate with sleeve-like holding-down means, not shown, which are fastened to the removable cover. The holding-down means surround the respective holding pin 20 and press the ratchet spring, which is arranged between the holding-down means and the base 10*a*, or the two tabs of the ratchet spring downwards against the base 10*a*. It is therefore possible to dispense with a screw connection for fixing the ratchet spring 12*b*. This also reduces the assembly costs.

Overall, the example of embodiment of FIG. 1 makes it possible to have a completely wireless socket structure. It is also possible to replace only some of the wiring by the mechanical connections, i.e. connections which are not produced by a material bond. For example, only the upper first connection means 13 may be used, whereas the connection between the second contact pin 23*b* and the ratchet spring 12*b* is configured in a different manner. Instead of the clip connections illustrated in FIG. 1, other mechanical connections, for example flexible tongues, may be provided which replace the clips individually or as a whole. The necessary contact pressure for the flexible tongues is achieved by clamping the cover with the housing. Instead of the clip connection of the second connection means 14, likewise a flexible tongue may be used which lies underneath against the second contact pin 23*b*.

With the example of embodiment of FIG. 1, completely tool-free assembly of the socket module is possible.

Since the socket module, as in EP 14 154 490, can be exchanged simply, in particular without a subsequent safety inspection, the socket module according to FIG. 1 is also disclosed and claimed in conjunction with a set together with a removal tool, as described in greater detail in the above-mentioned European patent application.

LIST OF REFERENCE NUMERALS

10 housing
10*a* base of the housing
11 first connector
11*a* first contact (connection)
11*b* second contact (connection)
12 second connector
12*a* first contact (female socket)
12*b* second contact (ratchet spring)
13 first connection means
13*a* first contact region (clip)
13*b* second contact region (clip)
14 second connection means
14*a* first contact region (clip)
14*b* second contact region (bearing surface)
15 printed circuit board
15*a*, *b* third contact region, contact means (clips)
16 metal strip
17 jaws
18 stop
19 outer edge
20 holding pin
21 free
22 screw
23*a*, 23*b* contact pins
24 holding edge
25 bent edge

What is claimed is:

1. An apparatus comprising a socket module comprising:
a housing (10),
at least two connectors (11, 12), individual ones of the at least two connectors including two contacts (11*a*, 11*b*, 12*a*, 12*b*) and at least a first connection means (13) which electrically connects a first contact (11*a*) of the first connector (11) to a first contact (12*a*) of the second connector (12),
wherein
the first connection means (13) has two contact regions (13*a*, 13*b*), of which a first contact region (13*a*) is connected to the first contact (11*a*) of the first connector (11) and a second contact region (13*b*) is connected to the first contact (12*a*) of the second connector (12), in positive manner and/or in non-positive manner in each case, and
a printed circuit board (15) is arranged in the housing (10), which board is electrically connected to the first connector (11), the printed circuit board (15) having a third contact region (15*a*, 15*b*) which connects the first connector (11) to the printed circuit board (15) in positive manner or in non-positive manner.

2. The apparatus according to claim 1, wherein the socket module further comprises a second connection means (14) electrically connecting a second contact (11*b*) of the first connector (11) to a second contact (12*b*) of the second connector (12), the second connection means (14) having two contact regions (14*a*, 14*b*), of which a first contact region (14*a*) is connected to the second contact (11*b*) of the first connector (11) in positive manner and/or in non-positive manner, and a second contact region (14*b*) is connected to the second contact (12*b*) of the second connector (12) in positive manner and/or in non-positive manner or by a material bond.

3. The apparatus according to claim 1, wherein the first connection means (13) is connected to the housing (10).

4. The apparatus according to claim 1, wherein the first connection means (13) is connected to a removable cover of the housing (10) and the second connection means (14) is connected to a base (10*a*) of the housing (10).

5. The apparatus according to claim 1, wherein the contact regions (13*a*, 13*b*) of the first connection means (13) form clips and/or flexible tongues which are latched with the first contacts (11*a*, 12*a*) and/or lie against them.

6. The apparatus according to claim 1, wherein the contact regions (14*a*, 14*b*) of the second connection means (14) form clips and/or flexible tongues and/or bearing surfaces which are latched with the second contacts (11b, 12b) and/or lie against them and/or are connected thereto by a material bond.

7. The apparatus according to claim 1, wherein the first connection means (13) forms a metal strip (16), on ends of which the contact regions (13a, 13b, 14a, 14b) are provided.

8. The apparatus according to claim 1, wherein the third contact region (15a, 15b) forms at least one clip which is connected to the printed circuit board (15).

9. The apparatus according to claim 1, wherein the contact regions (13a, 13b, 14a, 14b, 15a, 15b) have two jaws (17) arranged opposite one another, which in a holding state are acted upon by a spring force.

10. The apparatus according to claim 1, wherein the first connector (11) comprises a contact pin (23a, 23b) which has a stop (18) which cooperates with an outer edge (19) of the printed circuit board (15) to position the connector (11).

11. The apparatus according to claim 1, wherein the first connector (11) comprises two contact pins (23a, 23b) which form the first and second contact (11a, 11b) of the first connector (11).

12. The apparatus according to claim 1, wherein the second connector (12) comprises a female socket and a ratchet spring, the female socket forming the first contact (12a) and the ratchet spring the second contact (12b) of the second connector (12).

13. The apparatus according to claim 1, wherein the second connector (12) is placed on at least one holding pin (20) and is fixed by at least one sleeve-like holding-down means which surrounds the holding pin (20).

14. The apparatus according to claim 1 further comprising an electrosurgical device incorporating one or more of the socket module.

15. The apparatus according to claim 1 further comprising the socket module and a removal tool which has at least one unlocking bar with a free end.

16. An apparatus comprising a socket module comprising:
a housing,
at least two connectors, individual ones of the at least two connectors including two contacts and at least a first connection member configured to electrically connect a first contact of the first connector to a first contact of the second connector,
a printed circuit board arranged in the housing and electrically connected to the first connector,
wherein the first connection member supports two contact regions, of which a first contact region is connected to the first contact of the first connector and a second contact region is connected to the first contact of the second connector, in positive manner and/or in non-positive manner in each case, and
wherein the printed circuit board supports a third contact region configured to connect the first connector to the printed circuit board in positive manner or in non-positive manner.

17. The apparatus of claim 16, wherein the socket module further comprises a second connection member configured to electrically connect a second contact of the first connector to a second contact of the second connector, wherein the second connection member supports two contact regions, of which a first contact region is connected to the second contact of the first connector in positive manner and/or in non-positive manner, and a second contact region is connected to the second contact of the second connector in positive manner and/or in non-positive manner or by a material bond.

18. The apparatus of claim 16, wherein the contact regions of the first connection member form clips and/or flexible tongues configured to latch with the first contacts (11a, 12a) and/or lie against them.

* * * * *